US008831717B2

(12) United States Patent
Solem et al.

(10) Patent No.: US 8,831,717 B2
(45) Date of Patent: Sep. 9, 2014

(54) ESTIMATION OF PROPENSITY TO SYMPTOMATIC HYPOTENSION

(75) Inventors: Kristian Solem, Malmö (SE); Bo Olde, Lund (SE)

(73) Assignee: Gambro Lundia AB, Lund (SE)

(*) Notice: Subject to any disclaimer, the term of this patent is extended or adjusted under 35 U.S.C. 154(b) by 1494 days.

(21) Appl. No.: 12/441,921

(22) PCT Filed: Sep. 6, 2007

(86) PCT No.: PCT/SE2007/000775
§ 371 (c)(1),
(2), (4) Date: Dec. 22, 2009

(87) PCT Pub. No.: WO2008/036011
PCT Pub. Date: Mar. 27, 2008

(65) Prior Publication Data
US 2010/0094158 A1    Apr. 15, 2010

Related U.S. Application Data

(60) Provisional application No. 60/826,295, filed on Sep. 20, 2006.

(30) Foreign Application Priority Data

Sep. 19, 2006 (SE) ...................................... 0601928

(51) Int. Cl.
*A61B 5/05* (2006.01)
*A61B 5/053* (2006.01)
*A61B 5/03* (2006.01)

(52) U.S. Cl.
USPC ........... 600/547; 600/300; 600/301; 600/529; 600/533

(58) Field of Classification Search
USPC ............ 600/300, 301, 529, 533, 547; 606/17, 606/18
See application file for complete search history.

(56) References Cited

U.S. PATENT DOCUMENTS

| 4,710,164 A | 12/1987 | Levin et al. |
| 4,807,638 A | 2/1989 | Sramek |

(Continued)

FOREIGN PATENT DOCUMENTS

| WO | WO 02/13691 A1 | 2/2002 |
| WO | WO 2006/031186 A1 | 3/2006 |

OTHER PUBLICATIONS

Cai, Y. et al., "Can Haemodialysis-Induced Hypotension Be Predicted?", Nephron 2002, vol. 92, No. 3, pp. 582-588, (Sep. 2002).

(Continued)

*Primary Examiner* — Sean Dougherty
(74) *Attorney, Agent, or Firm* — Finnegan, Henderson, Farabow, Garrett & Dunner LLP

(57) ABSTRACT

The invention relates to estimation of a patient's propensity to suffer from symptomatic hypotension during extracorporeal blood treatment. An electromagnetic test signal, which is applied over a thoracic region of the patient via at least one transmitter electrode. A result signal produced in response to the test signal is received via at least one receiver electrode on the patient. A test parameter is derived based on the result signal. The test parameter expresses a fluid status of the thoracic region of the patient, and it is determined whether the test parameter fulfills an alarm criterion. If the test parameter fulfills an alarm criteria, an alarm signal is generated. This signal indicates that the patient is hypotension prone, and that appropriate measures should be taken.

13 Claims, 2 Drawing Sheets

(56) References Cited

U.S. PATENT DOCUMENTS

| | | | |
|---|---|---|---|
| 5,178,154 A * | 1/1993 | Ackmann et al. | 600/526 |
| 5,469,859 A * | 11/1995 | Tsoglin et al. | 600/536 |
| 5,749,369 A * | 5/1998 | Rabinovich et al. | 600/547 |
| 6,339,722 B1 * | 1/2002 | Heethaar et al. | 600/547 |
| 6,454,708 B1 * | 9/2002 | Ferguson et al. | 600/300 |
| 6,600,949 B1 * | 7/2003 | Turcott | 600/518 |
| 7,447,543 B2 * | 11/2008 | Belalcazar et al. | 600/547 |
| 7,474,918 B2 * | 1/2009 | Frantz et al. | 600/547 |
| 8,005,543 B2 * | 8/2011 | Libbus et al. | 607/9 |
| 2002/0147475 A1 | 10/2002 | Scheiner et al. | |
| 2002/0193689 A1 * | 12/2002 | Bernstein et al. | 600/454 |
| 2004/0172080 A1 | 9/2004 | Stadler et al. | |
| 2005/0137626 A1 | 6/2005 | Pastore et al. | |
| 2005/0215918 A1 * | 9/2005 | Frantz et al. | 600/547 |
| 2005/0283197 A1 | 12/2005 | Daum et al. | |
| 2006/0041280 A1 | 2/2006 | Stahmann et al. | |
| 2006/0058593 A1 * | 3/2006 | Drinan et al. | 600/301 |
| 2006/0184060 A1 * | 8/2006 | Belalcazar et al. | 600/547 |
| 2006/0241510 A1 * | 10/2006 | Halperin et al. | 600/534 |
| 2007/0156061 A1 * | 7/2007 | Hess | 600/547 |
| 2007/0208233 A1 * | 9/2007 | Kovacs | 600/300 |
| 2007/0260285 A1 * | 11/2007 | Libbus et al. | 607/9 |

OTHER PUBLICATIONS

Wynne, J. L. et al., "Impedance Cardiography: A Potential Monitor for Hemodialysis," Journal of Surgical Research, vol. 133, No. 1, pp. 55-60, (Jun. 2006).

Koziolek, M. J. et al., "Bioimpedance Analysis and Intradialytic Hypotension in Intermittent Hemodialysis," Clinical Nephrology, vol. 66, No. 1/2006, pp. 39-50, (Jul. 2006).

Nescolarde, L. et al., "Thoracic Versus Whole Body Bioimpedance Measurements: The Relation to Hydration Status and Hypertension in Peritoneal Dialysis Pateints," Physiol. Meas., vol. 27, No. 10, pp. 961-971, (Oct. 2006).

* cited by examiner

ESTIMATION OF PROPENSITY TO SYMPTOMATIC HYPOTENSION

CROSS REFERENCE TO RELATED APPLICATIONS

This application is a national phase application based on PCT/SE2007/000775, filed Sep. 6, 2007, which claims the priority of Sweden Patent Application No. 0601928-5, filed Sep. 19, 2006, and claims the benefit of U.S. Provisional Application No. 60/826,295, filed Sep. 20, 2006, the content of all of which is incorporated herein by reference.

THE BACKGROUND OF THE INVENTION AND PRIOR ART

The present invention relates generally to detection of the onset of a rapid drop in a patient's blood pressure in connection with extracorporeal blood treatments, such as hemodialysis (HD), hemofiltration (HF) or hemodiafiltration (HDF).

The human body consists of approximately 60% water—a level which is important to maintain for survival. While it is unproblematic to provide the body with new water, disposal of surplus water is a major problem in renal patients. The task of the normal kidney is to remove superfluous fluid from the blood, such as water, urea and other waste products. The resulting urine is transferred to the bladder and finally leaves the body during urination. The kidney's second task is to regulate for example the balance of acid and base. With malfunctioning kidneys, disorders may develop in most major body organs, a syndrome called uremia. If uremia remains untreated, it will lead to death. Uremia is treated either by kidney transplantation, or some form of blood treatment, extracorporeal or intracorporeal Due to extensive fluid extraction during extracorporeal blood treatment, it is common that the patient suffers from symptomatic hypotension, characterized by a blood pressure drop and symptoms such as cramps, nausea, vomiting and sometimes fainting. Such an event is not only strenuous for the patient, but also requires considerable attention from the staff overseeing the treatment. Consequently, when performing extracorporeal blood treatment, it is highly desirable to detect the onset of symptomatic hypotension and preventing it from coming about. Moreover, before initiating the treatment of a given patient, it is important to estimate whether or not this patient is especially inclined to encounter hypotension related problems, i.e. is hypotension-prone, so that the treatment parameters can be adapted appropriately.

In the article, "Can Haemodialysis-Induced Hypotension be Predicted?", Nephron 2002; 92:582-588, Cai, Y. et al. conclude that in HD patients hypotension is brought out by a reduction in the central blood volume. Namely, such a volume reduction, in turn, affects the heart rate and the distribution of red cells within the body unfavorably. The article suggests that HD-induced hypotension be prevented by reducing the ultrafiltration rate when an increase in the thoracic impedance approaches 5Ω, or when an admittance index of intracellular water decreases by $6 \cdot 10^{-4}$.

The published international patent application WO 2005/094498 discloses a solution for monitoring thoracic impedance by means of an electrode array. Here, it is stated that for instance renal disease correlates with the level and variation of the level of intrathoracic fluids. Nevertheless, no strategy is proposed by means of which this information is used to predict hypotension.

Hence, although relationships between the onset of hypotension and variations in the central blood volume/thoracic impedance have been discovered, no solution exists, which is capable of utilizing these relationships to identify dialysis patients being especially prone to suffer from symptomatic hypotension.

SUMMARY OF THE INVENTION

The object of the present invention is to accomplish a solution by means of which a patient's propensity to symptomatic hypotension can be estimated, and if necessary, measures can be taken in due time to prevent that the patient experiences a rapid blood pressure decrease and its undesirable effects.

According to one aspect of the invention, the object is achieved by the initially described alarm apparatus, wherein the analysis unit includes a processing module adapted to derive a test parameter based on the result signal. The test parameter expresses a fluid status of the thoracic region of the patient. For example, the test parameter may describe an extracellular-to-intracellular fluid ratio. The analysis unit also includes a comparison module adapted to test whether or not the test parameter fulfills an alarm criterion. If so, an alarm triggering module in the analysis unit is adapted to cause an alarm signal to be generated.

An important advantage attained by this apparatus is that an early and accurate determination is obtained regarding the hypotension risk for a particular patient in connection with a particular treatment. Thus, the staff may take adequate measures, and/or the treatment performed by the dialysis machine can be automatically adjusted in the light of a detected risk.

According to a preferred embodiment of this aspect of the invention, the electromagnetic test signal includes at least two signal components with mutually different spectral properties. Moreover, via the at least one receiver electrode, the input interface is adapted to receive a set of result signal components produced in response to the test signal. The processing module is adapted to derive the test parameter based on the set of result signal components. This strategy provides a robust and reliable implementation.

According to yet another preferred embodiment of this aspect of the invention, the test parameter expresses an extracellular-to-intracellular fluid ratio in the thoracic region of the patient. Here, the test parameter preferably reflects an admittance ratio calculated as a first admittance value divided by a second admittance value. The first admittance value expresses an estimate of a low-frequency response to a first signal component in the electromagnetic test signal. The second admittance value represents a difference between a high-frequency response to a second signal component in the electromagnetic test signal and the low-frequency response. Moreover, according to this embodiment, the comparison module is preferably adapted to deem the alarm criterion as fulfilled if the test parameter exceeds a first threshold value.

According to another preferred embodiment of this aspect of the invention, the test parameter expresses an extracellular fluid volume, and the alarm triggering module is adapted to deem the alarm criterion as fulfilled if the test parameter exceeds a second threshold value. Alternatively, the test parameter expresses an intracellular fluid volume, and the comparison module is adapted to deem the alarm criterion as fulfilled if the test parameter is below a third threshold value. Both these strategies accomplish reliable estimates of a dialysis patient's propensity to symptomatic hypotension According to still another preferred embodiment of this aspect of the invention, the first signal component has such spectral properties that its electromagnetic energy is distributed in a first frequency band extending from a lower first frequency limit to an upper first frequency limit. Analogously, the second signal component has such spectral properties that its electromagnetic energy is distributed in a second frequency band extending from a lower second frequency limit to an upper second frequency limit. Further, the lower second frequency limit represents a higher frequency than the upper first frequency limit, i.e. the first and second frequency bands are essentially non-overlapping. Of course, neither the first or the second signal component need to contain frequency components from the entire first and second frequency band respectively. In fact, one or both of the first and second signal components may represent singular periodic waves. Namely, such a separation in frequency enables efficient determination of the fluid status in the patient's thoracic region.

According to a further preferred embodiment of this aspect of the invention, the lower first frequency limit is approximately 1 kHz and the upper first frequency limit is approximately 10 kHz. Moreover, the lower second frequency limit is approximately 10 kHz and the upper second frequency limit is approximately 100 MHz. These ranges have proven to provide reliable bio-impedance values, and thus a consistent operation of the proposed apparatus.

According to another preferred embodiment of this aspect of the invention, the test signal includes a source signal component of a well-defined frequency. Moreover, the processing module is adapted to derive the test parameter based on a phase shift of the result signal relative to the source signal component and an attenuation of the result signal relative to the source signal component. Thereby, reliable bio-impedance values can be provided, and thus the proposed apparatus will operate consistently.

According to a further preferred embodiment of this aspect of the invention, the processing module is adapted to receive at least one physiology parameter expressing body specific features of the patient. Then, on the further basis of the at least one physiology parameter, the processing module is adapted to derive the test parameter. The at least one physiology parameter preferably includes body weight data, height data and/or data specifying a body fat content. Thereby, the test parameter can be normalized with respect to the size of the patient. Furthermore, since the body fat has a bio-impedance distinct from other body tissues, like muscles, it is important that this factor be compensated for in order to attain a highly accurate measure of the thoracic impedance.

According to still another preferred embodiment of this aspect of the invention, the processing module is adapted to receive a treatment specific parameter and/or a patient specific parameter. The treatment specific parameter specifies characteristics of the extracorporeal blood treatment, such as the temperature of the dialysis fluid, the ultrafiltration rate etc., and the patient specific parameter specifies vital signs of the patient, such as the pulse rate, the blood pressure, the body temperature, the respiratory rate etc. The processing module is adapted to derive the test parameter on the further basis of these parameters. Hence, the quality of the test parameter is improved.

According to another aspect of the invention, the object is achieved by a medical system including a dialysis machine adapted to perform extracorporeal blood treatment of the patient and the above-proposed alarm apparatus.

According to further aspect of the invention the object is achieved by the initially described method, wherein based on the result signal, a test parameter is derived. The test parameter expresses a fluid status of the thoracic region of the patient. It is tested whether or not the test parameter fulfills an alarm criterion, and if so, an alarm signal is caused to be generated. The advantages of this method, as well as the preferred embodiments thereof, are apparent from the discussion hereinabove with reference to the proposed alarm apparatus.

According to a further aspect of the invention the object is achieved by a computer program directly loadable into the internal memory of a computer, comprising software for controlling the above proposed method when said program is run on a computer.

According to another aspect of the invention the object is achieved by a computer readable medium, having a program recorded thereon, where the program is to make a computer control the above proposed method.

Further advantages, advantageous features and applications of the present invention will be apparent from the following description and the dependent claims.

BRIEF DESCRIPTION OF THE DRAWINGS

The present invention is now to be explained more closely by means of preferred embodiments, which are disclosed as examples, and with reference to the attached drawings.

DESCRIPTION OF PREFERRED
EMBODIMENTS OF THE INVENTION

Figure 1:
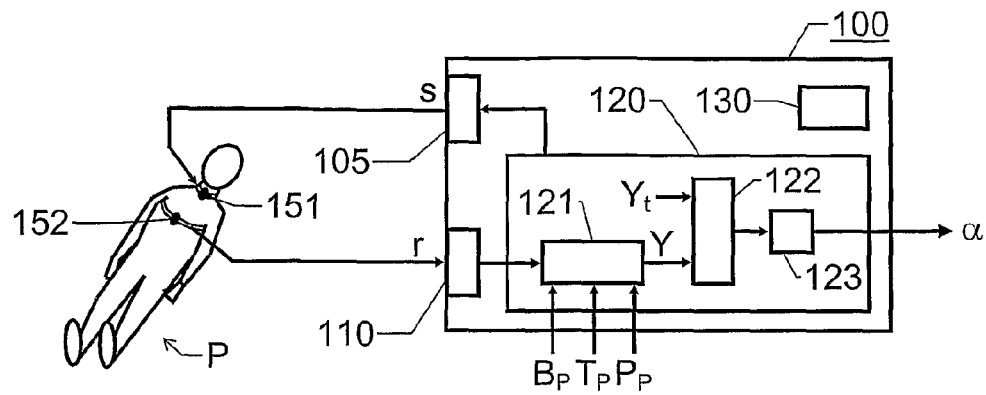
FIG. 1 shows a block diagram over an alarm apparatus according to one embodiment of the invention.

FIG. 1 shows a block diagram over an alarm apparatus 100 according to one embodiment of the invention for estimating a patient's P propensity to suffer from symptomatic hypotension during extracorporeal blood treatment. The apparatus 100 includes an output interface 105, an input interface 110 and an analysis unit 120.

The output interface 105 is adapted to generate an electromagnetic test signal s adapted to be fed to at least one transmitter electrode 151. This electrode 151, in turn, is adapted to be attached to the patient P, so that the test signal s can be applied over the patient's P thoracic region via the electrode 151. The electromagnetic test signal s either includes at least two signal components having mutually different spectral properties, or the test signal s includes a single source signal component having a well-defined frequency.

Figure 5:
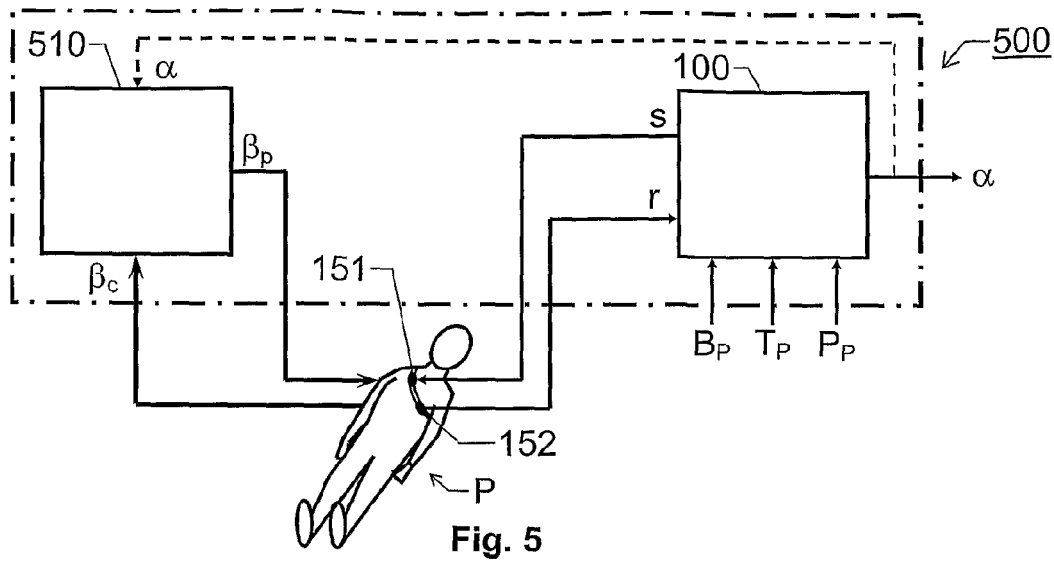
FIG. 5 shows a block diagram over a medical system according to one embodiment of the invention.

The input interface 110 is adapted to receive a result signal r produced in response to the test signal s. The result signal r is registered by at least one receiver electrode 152 on the patient's P body. It is advantageous if the electrodes 151 and 152 are integrated into textile bands. These bands can then be placed around the patient's P neck and torso (e.g. proximate to the arm pit) respectively. Otherwise, both electrodes 151 and 152 may be attached to a single band, however electrically isolated from one another, and the band be placed on the patient P, such that the band extends diagonally over the patient's P torso, a first electrode is located near the neck and a second electrode is located near the arm pit. This arrangement is illustrated in FIG. 5.

In any case, the textile bands may be elastic, such that a tension force sensor attached thereto can determine a degree of band extension, and thus estimate a body size of the patient P. Alternatively, the textile bands may be essentially non-elastic, and have a well-defined impedance per unit length. Thus, a circumference of the patient P along the band can be determined by means of an impedance sensor connected to the band. Hence, an alternative means to estimate a body size of the patient P is provided. Nevertheless, irrespective of the specific properties of the bands, these bands are isolated from the electrodes 151, 152 and the patient's P skin respectively.

The analysis unit 120, in turn, comprises a processing module 121, a comparison module 122 and an alarm triggering module 123. The processing module 121 is adapted to derive a test parameter Y based on the result signal r. The test parameter Y expresses a fluid status of the thoracic region of the patient P. Consequently, the test parameter Y is also a measure of the blood volume in this region. If the relative blood volume in the thoracic region becomes modified outside of a critical interval, the cardio-vascular system will not be capable of maintaining the blood pressure. Hypotension is therefore likely to occur. The critical limit and the given rate are patient specific parameters, which vary both between different patients and for a particular patient depending on his/her current physiological status. During extracorporeal blood treatment the relative blood volume in the thoracic region often varies due to input and output of large amounts of body fluids. The comparison module 122 is adapted to test whether or not the test parameter Y fulfills an alarm criterion, here symbolized by means of a value $Y_t$. It advantageous to study a floating average of the test parameter Y over a window, say 15 minutes long, of historic test parameter values. I.e. the alarm criterion is preferably tested against an average value of all the test parameters Y derived during a foregoing interval whose duration is defined by said window. If the alarm criterion is found to be fulfilled, the alarm triggering module 123 further adapted to cause an alarm signal $\alpha$ to be generated. The alarm signal $\alpha$ may result in that an acoustic and/or visual indication is produced, which is adapted to inform an operator of the apparatus 100 that it is deemed likely that the patient P soon suffers from symptomatic hypotension. Thus, the operator can take measures to avoid this situation, for instance interrupting an ongoing dialysis treatment, adjusting one or more parameters in a planned or ongoing treatment, injecting a NaCl solution into the patient via a venous drip chamber, orienting the patient in the Trendelenburg position, or giving the patient something to drink. Alternatively, or as a complement thereto, the alarm signal $\alpha$ may be fed as an input to a dialysis machine, so appropriate adjustment of the treatment parameters can be effected automatically.

Preferably, the apparatus 100 also includes, or is associated with, a computer readable medium 130, having a program recorded thereon, where the program is to make the control unit 120 operate as described above. Moreover, to modules 121, 122 and 123 are preferably implemented in software. Hence, two or more of the modules may be effected by a single physical means or unit.

According to one embodiment of the invention, processing module 121 in the processing module is adapted to receive at least one physiology parameter $B_P$ expressing body specific features of the patient P. The physiology parameters $B_P$, which may describe body weight data, height data and data specifying a body fat content, can either be derived from electrode measurements (as described above), or be entered explicitly (manually or automatically). In any case, according to this embodiment, the processing module 121 is adapted to derive the test parameter Y on the further basis of the at least one physiology parameter $B_P$. Specifically, the processing module 121 here normalizes the registered bio-impedance properties of the patient's P thoracic region with respect to the at least one physiology parameter $B_P$ when determining the test parameter Y.

It is further preferable if the processing module 121 is adapted to receive a treatment specific parameter $T_P$ specifying characteristics of the extracorporeal blood treatment, such as the temperature of the dialysis fluid or the ultrafiltration rate. Moreover, the processing module 121 may be adapted to receive a patient specific parameter $P_P$ specifying at least one vital sign of the patient P, such as the pulse rate, the blood pressure, the body temperature or the respiratory rate. The processing module 121 is then adapted to derive the test parameter Y on the further basis of the parameter $T_P$ and/or the parameter $P_P$. The processing module 121 is adapted to derive the test parameter on the further basis of these parameters. Hence, the quality of the test parameter is improved.

According to embodiments of the invention, the test parameter Y expresses an extracellular fluid status (ECV), an intracellular fluid status (ICV) or a combination thereof, and the bio-impedance based test parameter Y may reflect impedance as well as admittance values. Depending on which measure that test parameter Y expresses and if the parameter reflects an impedance or an admittance value, different decision criteria are applicable.

Figure 2:
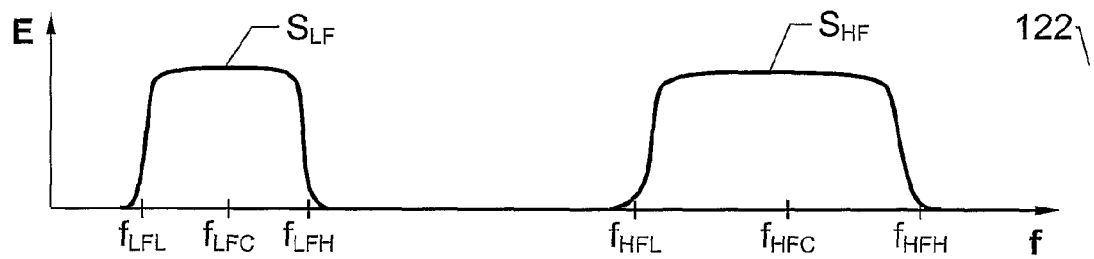
FIG. 2 shows a diagram illustrating the spectral properties of two test signal components employed according to a first embodiment of the invention.

According to one embodiment of the invention, the test parameter Y expresses an extracellular-to-intracellular fluid ratio, i.e. ECV/ICV, in the thoracic region of the patient P. Here, we assume that the electromagnetic test signal s includes a first signal component and a second signal component having frequency spectra $S_{LF}$ and $S_{HF}$ respectively as shown in FIG. 2. The first signal component has such spectral properties that its electromagnetic energy E is distributed in a first frequency band extending from a lower first frequency limit $f_{LFL}$ (say approximately 1 kHz) to an upper first frequency limit $f_{LFH}$ (say approximately 10 kHz). The second signal component has such spectral properties that its electromagnetic energy E is distributed in a second frequency band extending from a lower second frequency limit $f_{HFL}$ (say approximately 10 kHz) to an upper second frequency limit $f_{HFH}$ (say approximately 100 MHz). Moreover, the frequency spectra $S_{LF}$ and $S_{HF}$ are essentially non-overlapping, i.e. the lower second frequency limit $f_{HFL}$ represents a higher frequency than the upper first frequency limit $f_{LFH}$, however there may be a minor overlap with respect to the upper first frequency limit $f_{LFH}$ and the lower second frequency limit $f_{HFL}$.

In one embodiment of the invention, the test parameter Y reflects an admittance ratio and is calculated as:

$$Y = \frac{\frac{1}{Z_{LF}}}{\frac{1}{Z_{HF}} - \frac{1}{Z_{LF}}},$$

where $Z_{LF}$ expresses an impedance estimate based on a low-frequency response to the first signal component, and
$Z_{HF}$ expresses an impedance estimate based on a high-frequency response to the second signal component.

Figure 4:
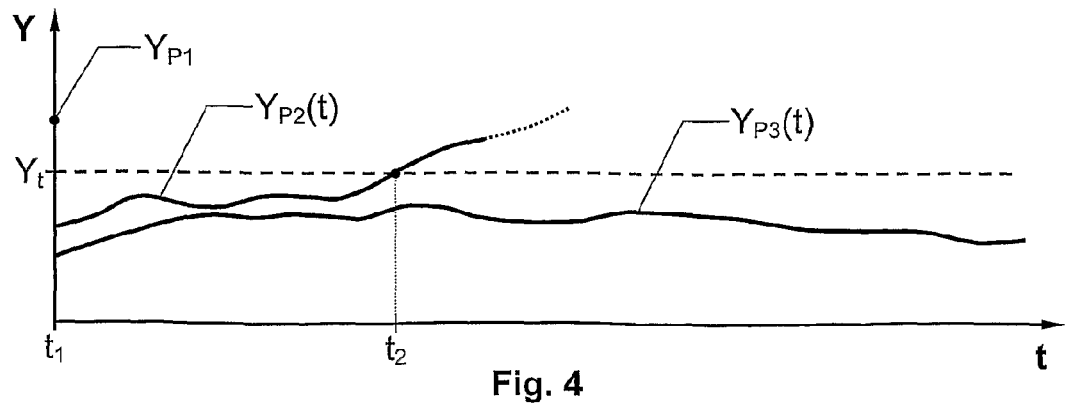
FIG. 4 shows a set of graphs exemplifying variations in the proposed test parameter in connection with extracorporeal blood treatment.

Furthermore, when testing the alarm criterion, the comparison module 122 is adapted to deem the alarm criterion as fulfilled if the test parameter Y exceeds a first threshold value $Y_t$. FIG. 4 shows a diagram with graphs exemplifying possible variations over time t in the proposed test parameter Y in connection with extracorporeal blood treatment of three different patients $Y_{P1}$, $Y_{P2}$ and $Y_{P3}$ respectively. The diagram in FIG. 4 also shows the first threshold value $Y_t$.

In this example, the test parameter $Y_{P1}$ in respect of a first patient is presumed to exceed the first threshold value $Y_t$ already at an initial point in time $t_1$. Hence, the alarm triggering module 123 immediately causes generation of the alarm signal α. In fact, it may be advantageous to perform the proposed testing well in advance of instigating the blood treatment, for instance in connection with registering and weighing the patient. In such a case, any alarm signal α would be generated even prior to the initial point in time $t_1$.

A second test parameter $Y_{P2}(t)$ in respect of a second patient is registered repeatedly as of the initial point in time $t_1$, and at all instances up until a second point in time $t_2$ the parameter falls below the first threshold value $Y_t$. However, at $t=t_2$, the second test parameter $Y_{P2}(t_2)$ exceeds the first threshold value $Y_t$. Consequently, then, the alarm triggering module 123 causes the alarm signal α to be generated. As a result, the blood treatment is aborted, be continued with adequately adjusted parameters, and/or continue after having taken other measures, e.g. injecting a NaCl solution into the patient via a venous drip chamber, orienting the patient in the Trendelenburg position, giving the patient something to drink etc.

Nevertheless, a third test parameter $Y_{P3}(t)$ repeatedly registered in respect of a third patient never exceeds the first threshold value $Y_t$. Therefore, no alarm signal α is generated in respect of this patient.

According to a first alternative to the above-described test parameter Y, the test parameter expresses an extracellular fluid volume in terms of an estimated admittance value. In this case, the comparison module 122 is adapted to deem the alarm criterion as fulfilled if the test parameter exceeds a second threshold value. Analogously, if an impedance representation of the extracellular fluid volume is selected, the alarm criterion will be regarded as fulfilled if the test parameter falls below a particular threshold value.

Figure 3:
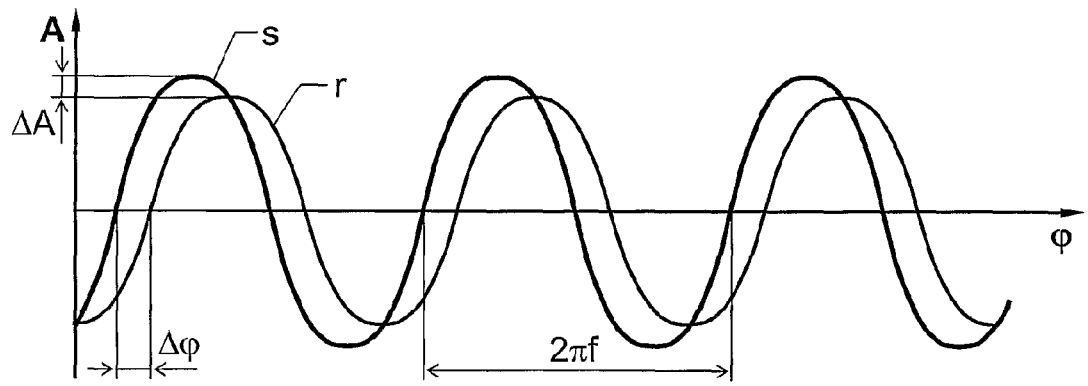
FIG. 3 shows a pair of graphs illustrating phase and amplitude differences between the test signal and the result signal detected according to a second embodiment of the invention.

According to a second alternative to the above-described test parameters, the test parameter expresses an intracellular fluid volume in terms of an estimated admittance value. Then, the alarm triggering module is adapted to deem the alarm criterion as fulfilled if the test parameter is below a third threshold value. Again, and analogous to the above, if an impedance representation of the extracellular fluid volume is selected, the alarm criterion will be regarded as fulfilled if the test parameter exceeds a particular threshold value FIG. 3 shows a diagram wherein a source signal component s of the test signal is represented. The source signal component s has a well-defined frequency f, and thus also a known wave-length 2πf. The frequency f preferably lies within a range from 1 kHz to 10 kHz. Moreover, the diagram in FIG. 3 represents a result signal r produced in response to the source signal component s, which is registered by the at least one receiver electrode 152 on the patient P. The result signal r is phase shifted Δφ relative to the source signal component s. The amount of phase shift Δφ is one indicator of the bio-impedance properties of the patient's P thoracic region. For a healthy subject the phase shift Δφ normally is in the order of 10°, whereas for a renal patient the phase shift Δφ may be as low as 2°. The result signal r is also attenuated in relation to the source signal component s, i.e. the result signal r has a smaller amplitude A than the source signal component s. In this example, the difference is ΔA. Besides said phase shift Δφ, the attenuation ΔA is an indicator of the bio-impedance properties of the patient's P thoracic region. According to one embodiment of the invention, the processing module 121 is adapted to determine the phase shift Δφ of the result signal r relative to the source signal component s, and determine the attenuation ΔA of the result signal r relative to the source signal component s. The processing module 121 is then adapted to derive the test parameter Y based on the phase shift Δφ and the attenuation ΔA.

FIG. 5 shows a block diagram over a medical system 500 according to one embodiment of the invention. The system 500 includes a dialysis machine 510 and the above-described alarm apparatus 100, which both are connected to a patient P. The dialysis machine 510 is adapted to perform extracorporeal blood treatment of the patient P, i.e. to process contaminated blood $β_c$ into purified blood $β_p$.

In parallel with cleaning the patient's P blood, the alarm apparatus 100 survey his/her propensity to symptomatic hypotension. In case of an alarm signal α, the overseeing staff can be informed and/or the dialysis machine 510 can be controlled to adjust its treatment parameter in order to avoid a hypotension situation.

This type of adjustment is symbolized by means of a dashed feedback signal α from the alarm apparatus 100 to the dialysis machine 510.

Figure 6:
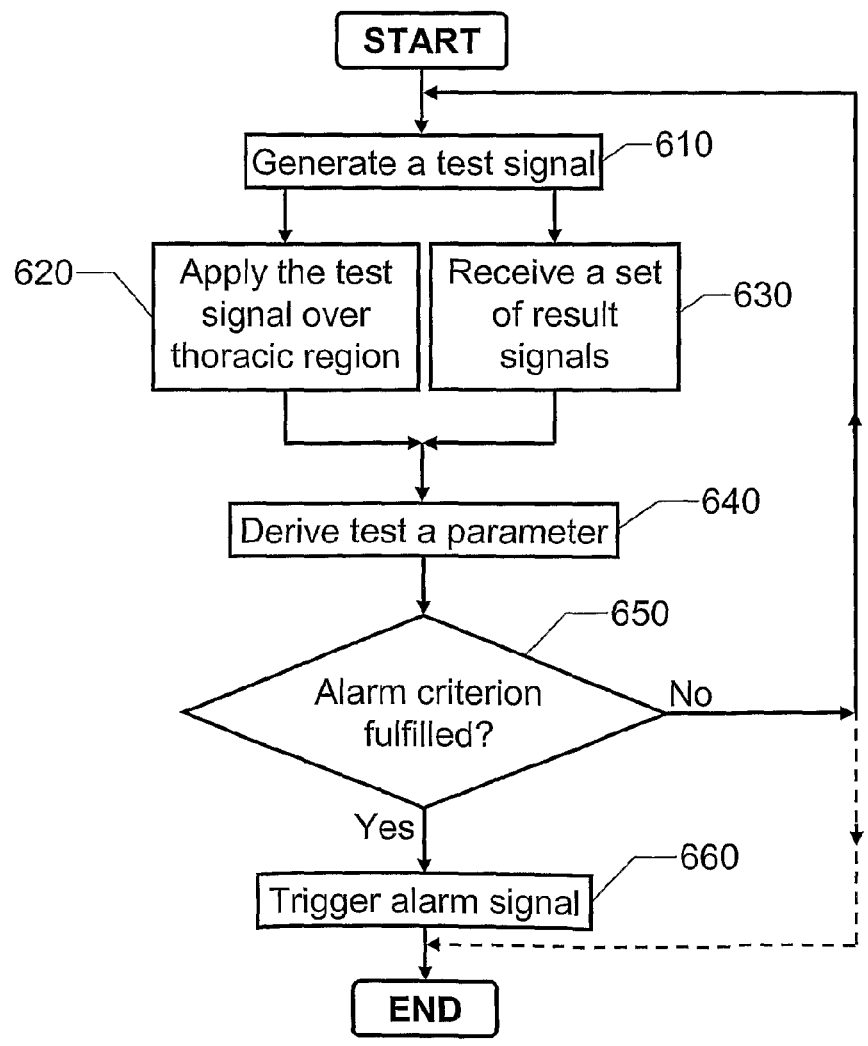
FIG. 6 shows a flow diagram which illustrates the general method according to the invention.

In order to sum up, the general method according to the invention will be described below with reference to the flow diagram in FIG. 6.

A first step 610 generates an electromagnetic test signal, which either has at least two signal components with mutually different spectral properties, or has a single source signal component of a well-defined frequency. Thereafter, a step 620 applies the test signal components over a thoracic region of the patient via at least one transmitter electrode. In parallel with that, a step 630 receives a set of result signals via at least one receiver electrode on the patient's body.

Subsequently, a step 640 derives a bio-impedance based test parameter from the set of result signals. The test parameter expresses a fluid status of the thoracic region of the patient. Then, a step 650 tests whether or not the test parameter fulfils an alarm criterion. If the alarm criterion is fulfilled, a step 660 follows. Otherwise the procedure may either loop back to the step 610 for generation of a new test signal, or end, depending on whether repeated surveillance of the patient is desired, or if a one-time testing is desired.

The step 660 causes an alarm signal to be generated. After that, the procedure ends.

All of the process steps, as well as any sub-sequence of steps, described with reference to the FIG. 6 above may be controlled by means of a programmed computer apparatus. Moreover, although the embodiments of the invention described above with reference to the drawings comprise computer apparatus and processes performed in computer apparatus, the invention thus also extends to computer programs, particularly computer programs on or in a carrier, adapted for putting the invention into practice. The program may be in the form of source code; object code, a code intermediate source and object code such as in partially compiled form, or in any other form suitable for use in the implementation of the process according to the invention. The carrier may be any entity or device capable of carrying the program. For example, the carrier may comprise a storage medium, such as a Flash memory, a ROM (Read Only Memory), for example a CD (Compact Disc) or a semiconductor ROM, an EPROM (Erasable Programmable Read- Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. An alarm apparatus for estimating a patient's propensity to suffer from symptomatic hypotension during extracorporeal blood treatment, the apparatus comprising:
    an output interface configured to generate an electromagnetic test signal, said electromagnetic test signal being configured to be fed to at least one transmitter electrode, said at least one transmitter electrode being configured to apply the test signal over a thoracic region of the patient;
    an input interface configured to receive a result signal via at least one receiver electrode on the patient's body, the result signal being produced in response to the electromagnetic test signal; and
    an analysis unit configured to determine a bio-impedance parameter based on the result signal, wherein the analysis unit comprises:
        a processing module configured to derive a test parameter based on the result signal, the test parameter expressing a fluid status of the thoracic region of the patient,
        a comparison module configured to test whether the test parameter fulfills an alarm criterion, and
        an alarm triggering module configured to cause an alarm signal to be generated if the alarm criterion is fulfilled, the electromagnetic test signal comprising at least two signal components with mutually different spectral properties, the input interface is adapted to receive a set of result signal components via the at least one receiver electrode, the set of result signal components being produced in response to the electromagnetic test signal, and the processing module is configured to derive the test parameter based on the set of result signal components.

2. The alarm apparatus according to claim 1, wherein the test parameter describes bio-impedance properties of the patient's thoracic region.

3. The alarm apparatus according to claim 1, wherein the test parameter expresses an extracellular-to-intracellular fluid ratio in the thoracic region of the patient.

4. The alarm apparatus according to claim 2, wherein the test parameter reflects an admittance ratio calculated as a first admittance value divided by a second admittance value, the first admittance value expressing an estimate of a low-frequency response to a first signal component in the electromagnetic test signal, and the second admittance value representing a difference between a high-frequency response to a second signal component in the electromagnetic test signal and the low-frequency response.

5. The alarm apparatus according to claim 3, wherein the comparison module is configured to deem the alarm criterion as fulfilled if the test parameter exceeds a first threshold value.

6. The alarm apparatus according to claim 2, wherein the test parameter expresses an extracellular fluid volume, and the comparison module configured to deem the alarm criterion as fulfilled if the test parameter exceeds a second threshold value.

7. The alarm apparatus according to claim 2, wherein the test parameter expresses an intracellular fluid volume, and the comparison module is configured to deem the alarm criterion as fulfilled if the test parameter is below a third threshold value.

8. The alarm apparatus according to claim 4, wherein the first signal component has spectral properties, including that the electromagnetic energy of the first signal component is distributed in a first frequency band extending from a lower first frequency limit to an upper first frequency limit,
    the second signal component has spectral properties, including that the electromagnetic energy of the second signal component is distributed in a second frequency band extending from a lower second frequency limit to an upper second frequency limit, and
    the lower second frequency limit represents a higher frequency than the upper first frequency limit.

9. The alarm apparatus according to claim 8, wherein the lower first frequency limit is approximately 1 kHz, the upper first frequency limit is approximately 10 kHz, the lower second frequency limit is approximately 10 kHz, and the upper second frequency limit is approximately 100 MHz.

10. The alarm apparatus according to claim 1, wherein the processing module is configured to:
    receive at least one physiology parameter expressing body specific features of the patient, and
    derive the test parameter on the further basis of the at least one physiology parameter.

11. The alarm apparatus according to claim 10, wherein the at least one physiology parameter comprises at least one of body weight data, height data, or data specifying a body fat content.

12. The alarm apparatus according to claim 1, wherein the processing module is configured to:
    receive at least one of a treatment specific parameter specifying at least one characteristics of the extracorporeal blood treatment, and a patient specific parameter specifying at least one vital sign of the patient; and
    derive the test parameter on the further basis of said at least one received parameter.

13. An alarm apparatus for estimating a patient's propensity to suffer from symptomatic hypotension during extracorporeal blood treatment, the apparatus comprising:
    an output interface configured to generate an electromagnetic test signal, said electromagnetic test signal being configured to be fed to at least one transmitter electrode, said at least one transmitter electrode being configured to apply the test signal over a thoracic region of the patient;
    an input interface configured to receive a result signal via at least one receiver electrode on the patient's body, the result signal being produced in response to the electromagnetic test signal; and
    an analysis unit configured to determine a bio-impedance parameter based on the result signal, wherein the analysis unit comprises:

a processing module configured to derive a test parameter based on the result signal, the test parameter expressing a fluid status of the thoracic region of the patient, a comparison module configured to test whether the test parameter fulfills an alarm criterion, and an alarm triggering module configured to cause an alarm signal to be generated if the alarm criterion is fulfilled, the electromagnetic test signal comprising at least two signal components with mutually different spectral properties, wherein one of the at least two signals is a source signal component of a frequency, and the processing module is configured to derive the test parameter based on a phase shift of the result signal relative to the source signal component and an attenuation of the result signal relative to the source signal component.

* * * * *